United States Patent [19]

Blasetti

[11] 4,128,344
[45] Dec. 5, 1978

[54] CENTRIFUGAL MIXER

[76] Inventor: David H. Blasetti, 7019 Guilford Rd., Upper Darby, Pa. 19082

[21] Appl. No.: 844,740

[22] Filed: Oct. 25, 1977

Related U.S. Application Data

[63] Continuation-in-part of Ser. No. 667,450, Mar. 16, 1976, Pat. No. 4,061,019.

[51] Int. Cl.$^2$ ............................................. B01F 9/02
[52] U.S. Cl. .................................... 366/348; 366/219
[58] Field of Search ..................... 366/219, 348, 349; 73/151, 715; 233/2

[56] References Cited

U.S. PATENT DOCUMENTS

| 2,301,967 | 11/1942 | Nosker | 73/151 |
|---|---|---|---|
| 2,822,127 | 2/1958 | Sinn | 233/2 |
| 3,679,184 | 7/1972 | Halliday | 366/219 |

FOREIGN PATENT DOCUMENTS 178780 6/1954 Austria.

*Primary Examiner*—Robert W. Jenkins
*Attorney, Agent, or Firm*—Dann, Dorfman, Herrell and Skillman

[57] ABSTRACT

Apparatus for mixing liquid or fluent material in which the material is confined within a carrier which is revolved about a remote axis to generate centrifugal forces directed radially outward from the remote axis. The carrier is also rotated about an axis perpendicular to the direction of the radial centrifugal force so that the force on any differential part of the material is cyclically reversed at a frequency determined by the frequency of the rotation about the perpendicular axis. The rate of rotation about the remote axis may be varied to vary the amplitude of the centrifugal force and the rate of rotation about the perpendicular axis may be varied to vary the frequency of the cyclic forces generated by this combination. The specific apparatus disclosed has a pair of elongated tubular rotary carriers which may be connected to receive liquid material from a supply. The carriers have their rotational axes parallel to one another and to the remote axis about which they revolve.

8 Claims, 3 Drawing Figures

CENTRIFUGAL MIXER

This application is a continuation-in-part of my copending U.S. application Ser. No. 667,450 filed Mar. 16, 1976, now Pat. No. 4,061,019.

The present invention relates to apparatus for generating cyclically-reversing forces in fluid material and is particularly applicable to a mechanism which combines predetermined rotary motions to produce controlled acceleration forces for the purpose of mixing the material.

The invention is useful for mixing liquids and fluid materials having a density at least as high as liquids and utilizes a carrier which is designed relative to the physical properties of the material to insure a mixing action when operating in a prescribed manner.

The invention operates by causing reversing flow within the body of material through the application of centrifugal forces first in one direction and then in the opposite direction, the reverse flows generating shear forces which cause the material to mix homogeneously.

Specifically, the invention provides a centrifugal mixer in which the fluid material is contained within a carrier and in which there need be no parts relatively movable during its operation.

The mixer of the present invention may effect both continuous-flow mixing and batch mixing, as required.

The objects of the invention are more fully set forth hereinafter with reference to the accompanying drawing, wherein.

Figure 1:
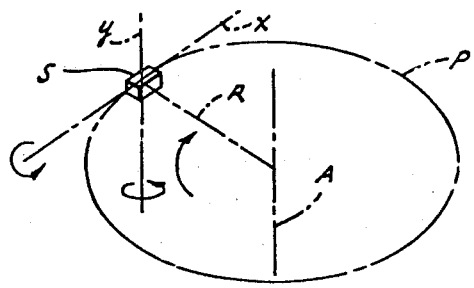
FIG. 1 is a diagram illustrating the mode of operation obtained by the present invention.

The generation of force components in the material is illustrated in FIG. 1. In FIG. 1, a body of fluid material is indicated by the reference character S. The body S is rotated about a remote central axis A, in the present instance, an axis spaced from the specimen by a radial length R. As the body S rotates about the axis at the distance R, a centrifugal force is generated resulting from the acceleration of the body as it travels in a circular path, for example the path indicated at P in FIG. 1. When the body rotates at a constant speed, for example an angular velocity of $\omega$, the acceleration forces generated in a radial direction are directly proportional to the square of the angular velocity ($\omega^2$) times the radius R, or, stated differently, the square of the tangential velocity ($v^2$) divided by R. The primary radial force component generated by the rotation of the body S about the axis A is directed outwardly.

The force applied at any point within the body is a differential force proportional to $\omega_1^2 R$ in an outward direction where $\omega_1$ is the angular velocity around the axis A and R is the distance of the part from the axis A. Since it is desired to mix the liquid, the body of liquid is rotated about an axis perpendicular to the radial force along the radius R. As shown in FIG. 1, the body may be rotated about an axis x tangential to the path P, about an axis y perpendicular to the path P or at any angle within the plane defined by the axes x and y. Rotating the body S about a perpendicular axis, for example the y axis, at an angular rate of $\omega_2$ revolutions per second causes the direction of the force applied to a differential mass of fluid to be reversed twice for each revolution, so that the speed of revolution of the body S about the secondary axis y determines the frequency of the mixing force generated in the mass.

The force generated by rotation about the secondary axis y is added to or subtracted from the primary force, depending upon the position of the differential mass of fluid in body S. In other words, as the body S rotates about the secondary axis, the centrifugal force generated on each differential mass of the body S by the rotation about the primary axis A varies cyclically between a maximum force directed away from the secondary axis to a maximum force directed toward the y axis, as each part within the body rotates about the y axis. This primary acceleration force is modulated by the secondary acceleration force about the y axis.

The same cyclic variation of the direction of application of the primary centrifugal force occurs regardless of the orientation of the secondary axis within the plane defined by the x and y axes, and regardless of the position of the secondary axis relative to the center of gravity of the body.

The force generated by the rotation of the part about the axis A is a constant centrifugal force which results from driving the body S about the circular path P. However, by reason of the body being rotated about a secondary axis y during the rotation about the axis A, the constant centrifugal force is cyclically varied in direction to produce a mixing force upon each differential part of the liquid body S. The liquid must be contained within a chamber which insures rotation of the liquid body about the respective axes.

In order to avoid centrifugal separation of the components of the liquid and obtain mixing of the liquid, the primary centrifugal force must exceed the secondary centrifugal force. The secondary force generated by rotation about the secondary axis y is adjusted relative to the primary force to provide optimum mixing. The maximum secondary force generated upon any differential part of the body is proportional to $\omega_2^2 r$; where $\omega_2$ is the angular velocity around the axis y, and r is the distance of the differential part from the y axis. To obtain the desired shear forces, $\omega_1^2 R$ must be greater than $\omega_2^2 r$. By controlling the secondary centrifugal force to be less than the primary force, the orientation of the net centrifugal force is determined by the orientation of the primary force. The orientation is outward from the primary axis A, but cyclically reverses relative to the secondary axis y. The cyclic reversal of the forces in the body S as it rotates about the y axis generates shear forces which effect a thorough mixing of the liquid which follows the rotation of the body about the y axis. The rotational speeds $\omega_1$ and $\omega_2$ may be adjustable where it is desired to accommodate the operation to materials having different physical properties. When the apparatus of the invention is designed to operate on a single given fluid material, the rotational speeds and the chamber sizes may be selected to conform to the physical properties of that material. The physical properties to be considered in selecting the proper rotational speeds and chamber sizes include the surface tension property, the viscosity, the density, and the frictional relationship between the elements of the carrier and the fluid material.

Figure 2:
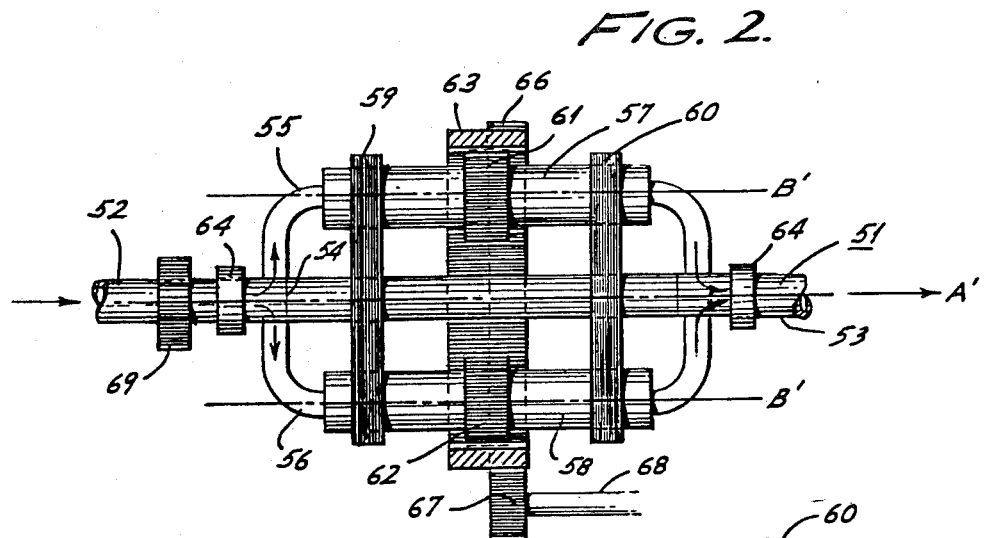
FIG. 2 is a view illustrating a mechanism embodying the present invention for mixing a liquid.
Figure 3:
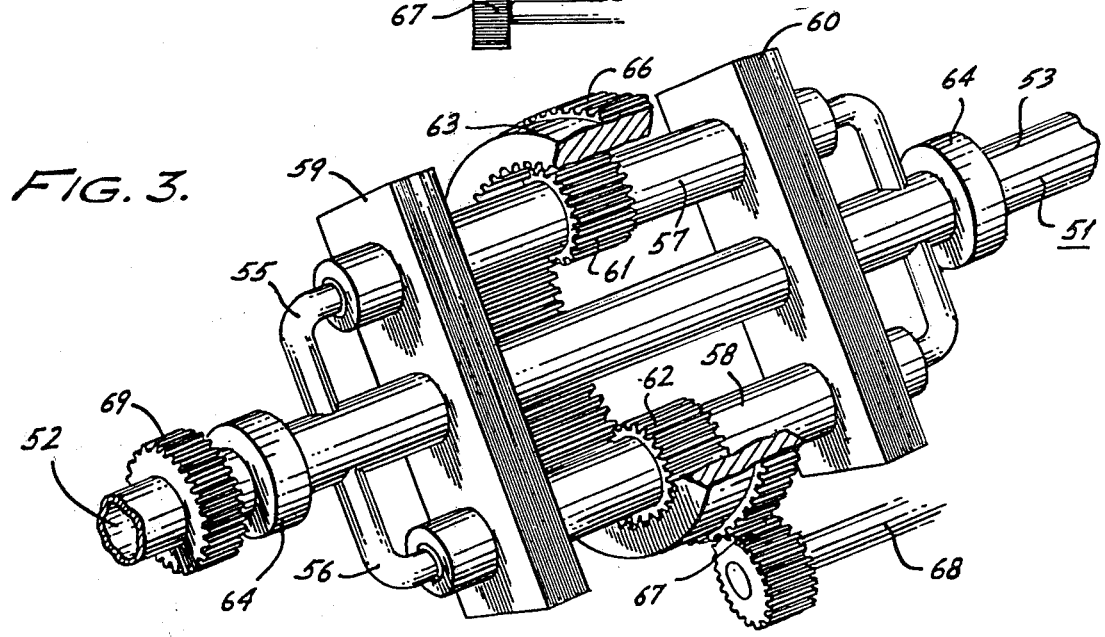
FIG. 3 is a perspective view of the structure shown in FIG. 2.

FIGS. 2 and 3 illustrate a suitable apparatus for imparting cyclically-reversing mixing shear forces to a fluid. In the present instance, the apparatus is designed to accommodate a fluid which is flowing through the apparatus as indicated by the arrows in FIG. 2, but it is also applicable to a batch process in which fluid is introduced into the apparatus as indicated by the first arrow and subjected to the mixing forces and then after mixing is withdrawn from the apparatus as indicated by the second arrow. While permitting axial flow of the liquid, the apparatus confines the liquid against radial flow arising from the centrifugal forces generated in operation of the mixing apparatus.

FIG. 2 illustrates apparatus comprising a hollow main shaft 51 which, in the present instance, is connected to a liquid supply at its lefthand end, as indicated at 52 and to a liquid discharge at 53. Between the supply and discharge ends 52 and 53, the shaft is plugged, as indicated at 54, so as to divert the liquid into branch conduits 55 and 56, extending outwardly respectively from opposite sides of the shaft 51. The branch conduits 55 and 56 lead into multiple elongated carriers or treatment chambers 57 and 58 which are disposed parallel to the main shaft 51 and are spaced radially therefrom, for example by mounting structures 59 and 60. In the present instance, the chambers have imperforate cylindrical walls confining the liquid therein against radial flow while permitting axial flow therethrough.

Each of the chambers 57 and 58 is rotatable within the structures 59 and 60 and has a planet gear 61 or 62, respectively, fixed thereon to drive the chambers about their individual axes. The planet gears 61 and 62 mesh with a ring sun gear 63 so that as the shaft 51 is rotated about its axis A', for example on bearings 64 adjacent the ends 52 and 53, the individual chambers 57 and 58 may be rotated about their axes B'. In the present instance, the ring gear 63 has external drive teeth 66 thereon which mesh with an external drive pinion 67 having a drive shaft 68 therefor. Thus, the rotation of the ring gear 63 may be controlled by the drive shaft 68 to either maintain the gear stationary or to drive it for concurrent or countercurrent rotation with the shaft 51. The rotation of the ring gear 63 controls the rotation of the chambers 57 and 58 about their respective axes B'. The shaft 51 is driven by a suitable gear 69 to cause the chambers 57 and 58 to rotate about the central axis A'. Thus, the apparatus of FIG. 2 operates to apply cyclically varying forces to the liquid within the chambers 57 and 58 in a manner as described with reference to the differential part of the liquid body S in FIG. 1, the axis A' in FIG. 2 corresponding to the axis A in FIG. 1, and the axis B' in FIG. 2 corresponding to the axis y in FIG. 1. In this way, the liquid, and any particle entrained therein, within either of the chambers 57 and 58 is subjected to cyclic forces determined by the angular rotation of the shaft 51 about its axis and at a frequency determined by the rotation of the chambers 57 and 58 about their respective axes B'.

The structure shown in FIGS. 2 and 3 has utility for subjecting liquids to forces which will mix homogeneously. The cyclically-varying forces applied to the liquid are effective to provide a thorough mixing of the liquid passing through the chambers 57 and 58. The magnitude of the force applied is proportional to the angular rotation of the device around the axis A' and the radial distance between the axes A' and B', and the cyclic frequency of the force is determined by the rotational speed of the chambers 57 and 58 about their respective axes.

Thus, in the illustrated embodiment, a body of liquid is subjected to cyclically-varying forces while in a carrier. The carrier is rotated about a first axis at a speed to generate a centrifugal force of a specified magnitude on each part of the body, and the carrier is rotated about a second axis perpendicular to the direction of the centrifugal force to effect cyclic variation of the orientation of the centrifugal force generated on each part.

The cyclically-varying forces on the different parts of the liquid body provide homogeneous mixture by a laminar shearing action. The walls of the carriers are smooth and the rotational speeds are high. Protrusions, deflector vanes, and paddles or other agitators inside the mixing chambers can be added to increase the turbulence and mixing action and reduce the rotational speeds necessary. Such agitators may be desired when mixing low-viscosity fluids to insure rotation of the body of fluid with the mixing chambers. While turbulent mixing may be faster, it could be less thorough.

Closed containers for the liquid may be used. Measured amounts of products are put into a container, and the container is closed with a lid, and then the container is rotated about two axes to mix the ingredients. The container may be devoid of interior protrusions or may have vanes mounted on its interior walls, or the lid can have vanes on it, whereby the product can be stirred after removal of the lid without the vanes being in the way.

In many cases, where the mixing was done by the batch, the process might easily be converted into a continuous mixing operation. There are other cases that seemed to inherently require batch operation. With careful design, some of these might be converted to continuous operation. In a reaction that first requires heat to get it going, and then cooling to keep the temperature under control, consideration should be given to the possibility of having the heating and cooling concurrent in controlled zones of a cylindrical mixer. The product would flow continuously through the zones, being mixed all the while.

In some cases, continuous operation simplifies the recycling of the output product.

In cases where the product may cake in the mixing carriers, the elements should be so constructed that all parts of it can be reamed clean, either by elimination of agitators or by mounting any agitators for easy removal for cleaning of the carriers.

If heating or cooling is required, the rotating parts considerably complicate connections to jackets on the mixing cylinders. The simplicity of the structure and the absence of relatively movable parts permits the entire apparatus to be put in a water shower, or a steam bath. Alternatively, the mixing may be done in stages, with two or more mixers, or recycling back into the same mixer. The heating or cooling would then be done between stages.

It is expected that control over the two spinning actions will give a greater range of mixing conditions so that a single mixer can be used to produce a larger variety of products than present equipment can.

The rate of mixing is believed proportional to the power input to the machine. A dynamometer may be attached to the driving means to show the power input. The machine operator can then control the operating conditions by watching a plot of the power absorbed by the mixer. The plot is relatively linear while laminar shearing is taking place. A sharp increase in power absorbed indicates the onset of turbulence. Conceivably, as the mixer speed is further increased, the power could drop, indicating loss of effectiveness due to improper mixing conditions.

While particular embodiments of the present invention have been herein illustrated and described, it is not intended to limit the invention to such disclosures, but changes and modifications may be made therein and thereto within the scope of the following claims.

I claim:

1. Apparatus for generating cyclically-reversing forces in a body of liquid comprising an elongated tubular chamber for carrying the liquid, means to revolve the chamber in a circular path about a first axis at a given angular speed, whereby a primary centrifugal force radial to said first axis is generated by each part of the liquid, a central hollow shaft coaxial with said first axis, support bearing means rotatably supporting said shaft, said revolving means operable to rotate said shaft, means mounting said chamber on said shaft for rotation about a second axis perpendicular to the direction of the primary centrifugal force whereby upon rotation of said hollow shaft said chamber moves in said circular path, drive means for effecting said rotation of said chamber on said second axis at an angular speed to produce a secondary centrifugal force in said part less than said primary centrifugal force, the direction of the net force being determined by the orientation of the part relative to said secondary axis, to thereby cyclically reverse the orientation of the net centrifugal force generated by each part in the body, relative to said second axis, a branch conduit communicating with said hollow shaft at one end and connected to said chamber at its other end, said chamber having an imperforate circumferential wall retaining said liquid in said carrier against said centrifugal forces.

2. Apparatus for generating cyclically-reversing forces in a fluid comprising multiple carriers for the fluid, means to rotate the carriers about a first axis at a given angular speed, whereby a primary centrifugal force radial to said first axis is generated by each part of the fluid, means for effecting rotation of each of said carriers about a second axis perpendicular to the direction of the radial centrifugal force at an angular speed to produce a secondary centrifugal force in said part less than said primary centrifugal force, the direction of the net force in said part being determined by the orientation of said part around said second axis to thereby cyclically reverse the orientation of the centrifugal force generated by each part of the fluid in said carrier, each carrier having an imperforate circumferential wall retaining said fluid within said carrier against said centrifugal forces.

3. Apparatus according to claim 2 wherein said carriers are elongated tubular chambers and are disposed equidistant from said first axis with their longitudinal axes parallel to said first axis, the longitudinal axis of each carrier being coaxial with said second axis.

4. Apparatus according to claim 3 wherein said carriers include planet gears, and a ring gear meshed with said planet gears so that as said carriers revolve about said first axis, said ring gear drives the planet gears to rotate each of said carriers about its longitudinal axis.

5. Apparatus according to claim 4 wherein said ring gear is mounted for rotation about said first axis, and including means to drive said ring gear independently of the rotation of said carriers.

6. A method of mixing a continuously-flowing liquid by generating cyclically-reversing forces in parts of said liquid comprising the steps of flowing said liquid through a chamber, revolving the chamber about a first axis at a given angular speed whereby a primary centrifugal force radial to said first axis is generated by each part of the liquid, rotating said chamber about a second axis perpendicular to the direction of the primary centrifugal forces in each part at an angular speed to produce a secondary centrifugal force in said part less than said primary centrifugal force, the direction of the net force being determined by the orientation of the part relative to said secondary axis so that as said chamber rotates about said second axis, said liquid, while rotating with said chamber, in each part generates forces which cyclically reverse in direction relative to the second axis.

7. A method according to claim 6 including the step of providing within the liquid, elements carried by said rotating chamber to insure rotation of the liquid as the chamber rotates about its axis.

8. A method according to claim 6, including the step of confining said liquid in said chamber to limit flow of liquid radial to said first axis while permitting flow parallel to said first axis.

* * * * *